United States Patent [19]

Ward

[11] 4,396,790
[45] Aug. 2, 1983

[54] LIGHT OLEFINIC HYDROCARBON ISOMERIZATION PROCESS

[75] Inventor: Dennis J. Ward, South Barrington, Ill.

[73] Assignee: UOP Inc., Des Plaines, Ill.

[21] Appl. No.: 333,081

[22] Filed: Dec. 21, 1981

[51] Int. Cl.³ .............................................. C07C 5/23
[52] U.S. Cl. .................................. 585/664; 585/668; 585/670
[58] Field of Search .............. 585/664, 665, 666, 667, 585/668, 669, 670

[56] References Cited

U.S. PATENT DOCUMENTS

| | | | |
|---|---|---|---|
| 2,387,994 | 10/1945 | Hillyer | 585/668 |
| 3,236,908 | 2/1966 | Sanford et al. | 585/668 |
| 3,800,003 | 3/1974 | Sobel | 260/683.49 |
| 3,821,123 | 6/1974 | Germanas et al. | 252/439 |
| 4,008,289 | 2/1977 | Ward et al. | 260/671 R |
| 4,104,321 | 8/1978 | Ward | 260/677 A |
| 4,217,461 | 8/1980 | Ward | 585/668 |

*Primary Examiner*—Delbert E. Gantz
*Assistant Examiner*—Anthony McFarlane
*Attorney, Agent, or Firm*—James R. Hoatson, Jr.; John F. Spears, Jr.; William H. Page, II

[57] ABSTRACT

A hydrocarbon conversion process for light olefin isomerization is disclosed. The feed stream is admixed with the overhead vapor stream of a fractionation column, which also acts as a feed stream drying column. The resultant admixture flows through an isomerization zone, and the isomerization zone effluent is partially condensed and passed into the overhead receiver of the column. Uncondensed vapor from the overhead receiver is recycled to the isomerization zone as a hydrogen recycle stream and liquid hydrocarbons withdrawn from the receiver are charged to the top of the fractionation column as the feed stream to the column.

7 Claims, 1 Drawing Figure

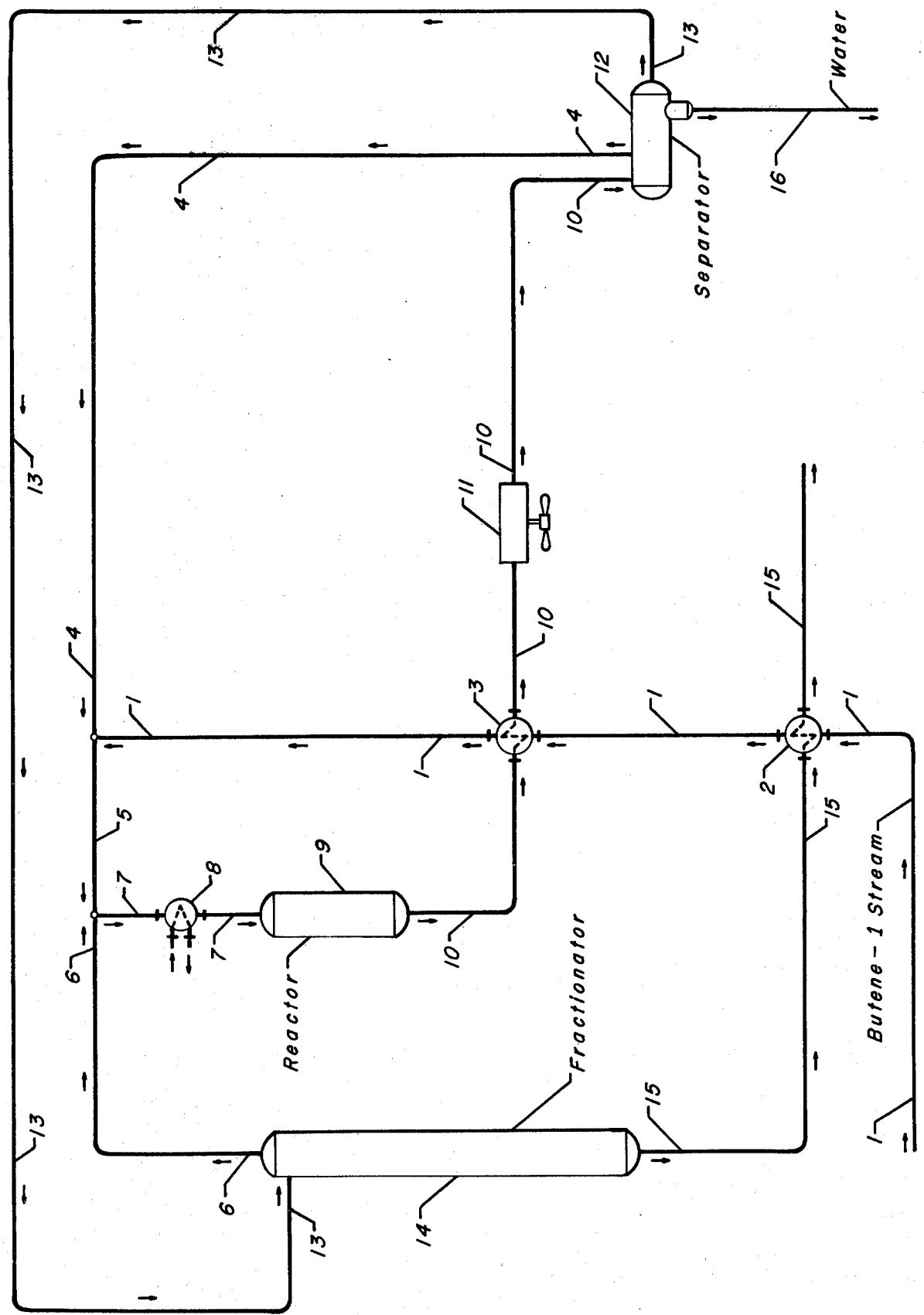

LIGHT OLEFINIC HYDROCARBON ISOMERIZATION PROCESS

FIELD OF THE INVENTION

The invention relates in general to a hydrocarbon conversion process. The invention more specifically relates to a process for the isomerization of hydrocarbons. The invention is specifically directed to a process for the isomerization of light normal olefinic hydrocarbons having from 4 to 7 carbon atoms per molecule.

PRIOR ART

It is a well known commercial practice to introduce a water containing hydrocarbon stream into the overhead system of a drying column to remove the water from the hydrocarbon stream. The hydrocarbon stream may be passed onto the top tray of the drying column or into the overhead receiver of the column as shown in U.S. Pat. No. 4,008,289.

The isomerization of normal olefinic hydrocarbons is described in U.S. Pat. No. 3,821,123. This reference describes the preferred catalyst for use in the isomerization of butene-1 to butene-2. The reference also discusses an isomerization process utilizing the catalyst and includes a description of the olefinic hydrocarbons which may be processed and suitable reaction conditions.

U.S. Pat. No. 4,104,321 discloses a process for the separation of light olefinic hydrocarbons which utilizes a fractionation column and two olefin isomerization reaction zones. The overhead stream of the fractionation column is passed into one of the isomerization zones. However, the process flow of the subject process differs substantially from that described in this reference. The reference is believed not to address the removal of water from the feed stream to the process.

U.S. Pat. No. 4,217,461 also presents a process for the isomerization of light olefinic hydrocarbons. This reference discloses the admixture of a feed stream comprising butene-1 with a recycle stream comprising hydrogen and a recycle stream comprising butene-2 and the passage of the resultant admixture into the first of two butene isomerization zones operated in series flow. The effluent of the second isomerization zone is passed into a vapor-liquid separation zone with the hydrogen-containing recycle stream being withdrawn from this vapor-liquid separation zone. The hydrocarbon liquid stream removed from this separation zone is passed into a fractionation column and the overhead stream of this fractionation column is returned to the isomerization zone as the recycle stream which comprises butene-1.

U.S. Pat. No. 3,800,003 discloses a process wherein a feed stream comprising a mixture of different butylenes is combined with a recycle stream comprising butene-1 and isobutylene and is then passed into an isomerization reactor. The effluent of the isomerization reactor is passed into a fractionator which concentrates the product butene-2 into a bottoms stream. This bottoms stream is then passed into a downstream alkylation zone for reaction with isobutane for the production of motor fuel.

BRIEF SUMMARY OF THE INVENTION

The invention provides a novel process for the isomerization of light normal olefinic hydrocarbons. The novel process of the subject invention is especially suited for use with a water-containing feed stream when it is desired to prevent the passage of excessive amounts of water into downstream processing operations. To this end the subject invention employs a single fractionation column and overhead system which acts as both the drying column of a butylene feed stream and as the product separation column of the isomerization zone effluent stream. The subject process is therefore distinguishable from the prior art by the placement of the isomerization zone in an upstream point of the overhead system of a feed stream drying column and by the passage of the feed stream into the isomerization zone rather than into the overhead separator or some other point in the overhead system. Other distinguishing features will be apparent to those skilled in the art.

One embodiment of the invention may be characterized as a hydrocarbon conversion process which comprises the steps of passing a feed stream which comprises water and a first olefin, a hydrogen recycle stream and a fractionation column overhead stream into an isomerization zone and thereby forming an isomerization zone effluent stream comprising a second olefin which is an isomer of the first olefin; partially condensing and then separating the isomerization zone effluent stream into a vapor phase stream comprising hydrogen, a liquid phase water stream and a liquid phase hydrocarbon stream comprising the first and the second olefin; passing at least a portion of the vapor phase stream into the isomerization zone as the hydrogen recycle stream; withdrawing the water stream from the process; and passing the liquid phase hydrocarbon stream into a fractionation zone wherein the liquid phase hydrocarbon stream is separated into the fractionation column overhead stream and a fractionation column bottoms stream which is rich in the second olefin. The process is preferably utilized to isomerize butene-1 to butene-2.

BRIEF DESCRIPTION OF THE DRAWING

The drawing illustrates the preferred embodiment of the invention. This representation of one embodiment is not intended tp preclude from the scope of the inventive concept those other embodiments disclosed herein or which result from the reasonable and expected modification to those embodiments which may be made by those skilled in the art. For purposes of simplicity and ease of understanding, many pieces of apparatus which are required for the successful operation of the process, such as pumps, compressors, process control equipment, reboilers and flow control valves, etc., have not been shown.

Referring now to the drawing, a feed stream which is preferably rich in butene-1 but which is also expected to contain significant and differing quantities of other butylenes including butene-2 and isobutylene enters the process through line 1. This feed stream contains a significant and perhaps variable amount of water derived from an upstream process or picked up during transportation or storage. The feed stream is heated in the indirect heat exchange means 2 and 3 and is then admixed with a hydrogen recycle stream carried by line 4. This admixture of the feed stream and hydrogen is then carried by line 5 to the point of admixture with the fractionation column overhead stream carried by line 6. The materials from lines 5 and 6 flow into line 7 and are heated to the desired isomerization temperature in an indirect heat exchanger means 8. The hydrogen-hydrocarbon mixture then continues through line 7 and enters an isomerization zone which preferably is contained within a single reactor 9. The entering hydrocarbons are contacted with an isomerization catalyst at effective olefin isomerization conditions and a significant portion of the butene-1 which enters the reactor is thereby converted to butene-2.

The effluent of reactor 9, which is also referred to herein as the isomerization zone effluent stream, is carried through the indirect heat exchange means 3 by line 10. This stream is then further cooled by the cooler 11 and passed into a vapor-liquid separator 12. The separator is designed and operated to effectively separate the entering mixed phase stream into a vapor stream removed through line 4 which comprises the hydrogen and other vapor phase components of the cooled reactor effluent stream. The liquid phase components of the reactor effluent stream carried by line 10 are separated into an aqueous phase which is withdrawn from the process as a water stream carried by line 16 and a less dense hydrocarbon phase comprising an admixture of butene-1, butene-2 and other hydrocarbons originally present in the feed stream.

The hydrocarbon phase is continuously withdrawn from the separator as a hydrocarbon stream carried by line 13 and passed into a fractionation zone. Preferably this fractionation zone comprises a single fractionator 14 and the hydrocarbon stream enters the top of this fractionation column. The fractionation column is designed and operated in a manner which separates the entering hydrocarbon streams into an overhead vapor stream carried by line 6 which contains a mixture of the entering $C_4$ hydrocarbons and substantially all of the water which was dissolved in the hydrocarbon stream carried by line 13 and a net bottoms stream carried by line 15. It is preferred that the net bottoms stream is rich in butene-2 or the corresponding product of the isomerization reaction carried out in the reactor.

DETAILED DESCRIPTION

There is often an imbalance between the need for a certain olefin isomer as a feedstock to a petroleum or petrochemical process and the available supply of that particular isomer. This may result when a particular olefinic isomer is used as the preferred feedstock of the process or when the olefin-consuming reaction is very specific and only one isomer is consumed or is preferentially consumed in the reaction of the process. For instance, it is normally desired to utilize butene-2 as the olefin feedstock in an HF-catalyzed alkylation process wherein a $C_4$ olefin is reacted with isobutane to produce high octane number gasoline blending components since this results in a superior quality alkylate than the alkylation of butene-1. Another example is the etherification reaction between methanol and isobutylene, with this reaction being essentially totally selective for isobutylene despite the presence of other $C_4$ olefins. Yet another example is the desire to utilize specific olefins as the feedstock to oligomerization or polymerization reactions. Butene-2 is also consumed in the production of several chemicals which are widely used or are themselves consumed in other chemical products including various plastics and solvents. Some of the more widely used chemicals produced from butene-2 are sec-butyl alcohol, maleic anhydride, butadiene and methylethyl ketone. It is therefore often necessary to eliminate the imbalance between the need and supply for a specific olefinic hydrocarbon by isomerization of available olefins into the desired olefin.

The feed stream to an isomerization process is often derived from a source which causes the feed stream to contain a significant amount of water. For instance, this water may be the result of the transportation of the feed stream material or the storage of the feed stream material in vessels which contained liquid water as the result of condensation, cleaning operations or the use of water as ballast. The feed stream may also be derived from a process in which it was in contact with water and therefore normally contains an equilibrium amount of water. For instance the feed olefin stream could be removed from the overhead receiver of a fractionation column in which liquid phase water is also present. Another potential source of an olefin-containing feed stream is the "inert" hydrocarbon effluent stream of an etherification reaction zone such as a zone in which a stream of mixed $C_4$ olefins is admixed with methanol and contacted with an etherification catalyst with the resultant selective reaction of the isobutylene contained in the $C_4$ feed stream with methanol. The other $C_4$ olefins pass through the reaction zone unaffected and are normally separated into a $C_4$ stream which is removed from the process and then water washed to recover methanol. This feed stream would be expected to contain water due to the water washing step used to recover methanol.

It is an objective of the subject invention to provide a process for the isomerization of olefinic hydrocarbons. It is a further objective of the present invention to provide a process for the isomerization of light acyclic olefinic hydrocarbons. A specific objective of the invention is to provide a process for the isomerization of water-containing butene-1 streams which produces a product stream having an increased concentration of butene-2 and an acceptably low water content.

The subject invention may be applied to the isomerization of any olefinic hydrocarbon which would normally be separated into a component of the overhead stream of a fractionation column which is utilized to separate this olefinic hydrocarbon from its other isomeric forms. The preferred feed is a light olefinic hydrocarbon. As used herein, the term "light" is intended to indicate a hydrocarbon containing from 4 to 6 carbon atoms per molecule. The preferred feed materials are butenes and amylenes with the conversion of butene-1 to butene-2 being the most highly preferred usage of the inventive concept.

The subject process has the advantage of performing the desired isomerization at a comparatively very low incremental cost over only removing water from the feed stream in a conventional drying column. That is, the added utility and capital costs of isomerizing the olefins in the subject process is much less than building and operating separate feed stream drying and olefin isomerization units. A large part of this cost reduction results from the fact that the isomerization zone is inserted into the middle of the equipment used to dry the feed stream. This eliminates duplication of equipment and utility costs. For instance the latent heat of vaporization of the overhead vapor stream of the drying column, which also serves as the isomerate product fractionator, is not removed until downstream of the isomerization zone. This means heat put into the process in the fractionator reboiler is also utilized to warm and vaporize the feed stream to the isomerization zone. The cooling which occurs downstream of the isomerization zone is both the required cooling of the fractionator overhead vapor stream and the cooling of the reactor effluent stream. This reduces the required number of heat exchangers compared to performing these cooling steps independently as parts of different processes. Another example of the capital cost reduction is shown by the same vessel functioning as the overhead separator of the column and as the product or vapor-liquid separator of the isomerization reactor. The savings that result from these duplications of function include a similar reduction or elimination of all other accouterments of a process such as valves, pumps and control systems.

The subject process is preferably used in conjunction with the distillation drying of the feed stream, but it can be performed with a dry feed stream which does not require water removal. The feed stream therefore preferably comprises water, with typical water concentrations being less than 1.0 mole percent. This small concentration of water can often have very deleterious effects on catalysts, absorbents, etc., and would be considered a significant contaminant even at a concentration of about 0.5 mole percent. The feed stream will normally be a mixture of various hydrocarbons in addition to the particular hydrocarbons which it is desired to isomerize. However, it is preferred that the feed stream is rich in compounds having the same carbon number as the feed hydrocarbon. As used herein the term "rich" is intended to indicate that the molar concentration of the specified chemical compound or class of compounds is greater than 50 percent. It is greatly preferred that at least 90 mole percent of all hydrocarbons in the feed stream have the same or the adjacent number of carbon atoms per molecule. The feed stream may often contain a relatively small amount of the single feed isomer. For instance, a typical feed stream to a butene-1 isomerization unit may only contain 10 mole percent butene-1. Another suitable feed stream is a mixture of $C_3$ and $C_4$ hydrocarbons derived from a fluidized catalytic cracking unit and containing a total of about 55 mole percent $C_4$ hydrocarbons.

The flow of the subject process is preferably similar to that shown in the Drawing. This flow includes heating the feed stream with heat recovered from the fractionation column bottoms stream and then with heat recovered from the isomerization zone effluent stream. These two preferred heat exchange steps could be deleted if desired, and additional heat exchange steps not shown on the Drawing could be employed instead of or in addition to these heat exchange steps. For instance, available heat in the reaction zone effluent stream could be used to reboil the fractionation column. In other possible variations process streams other than the feed stream could be heat exchanged against the net fractionator bottoms stream and reaction zone effluent stream to recover useful heat. The flow of the subject invention preferably includes the passage of the entire overhead vapor stream of the fractionation column into the isomerization zone without any intermediate cooling, condensation or separation.

Also passed into the isomerization zone is a vapor stream removed from the vapor-liquid separator. This recycle vapor stream is preferably rich in hydrogen and will contain substantially all of the hydrogen present in the isomerization zone effluent stream except for the hydrogen dissolved in the liquid removed from the separator or removed from the process as part of any off gas stream. The vapor stream will also contain an equilibrium mixture of all of the components of the isomerization zone effluent stream, and the composition of the separator off-gas vapor stream is therefore set by the conditions of temperature and pressure at which the separator is operated. In addition to hydrogen, the off-gas stream is expected to contain water vapor, both the feed and product olefinic hydrocarbons, other hydrocarbons present in the feed stream and their corresponding isomers and isomerization reaction by-products. It is anticipated that it will normally be necessary to remove a small portion of the off-gas vapor stream from the process as a drag stream to prevent the accumulation of excessive amounts of inert gases and highly volatile hydrocarbons within the recycle gas.

It is preferred that the total liquid-phase hydrocarbon stream withdrawn from the vapor-liquid separator is passed into a fractionation zone which comprises a single fractionation column. However, the fractionation zone could comprise two fractionation columns in such instances as a requirement to split the material entering the fractionation column into two or more effluent streams or a desire to utilize "superfractionation" to produce a very highly purified bottoms stream containing only one of the two isomers entering the column. The hydrocarbon liquid stream of the separator is preferably passed into the top of a single column as the only feed stream entering that column. This liquid stream serves as both the feed and reflux stream to this column. If two or more columns are utilized in the fractionation zone, then the hydrocarbon liquid stream is fed to the top of the column which has the most volatile components concentrated in its overhead vapor stream.

A preferred embodiment of the invention may be characterized as a butene isomerization process which comprises passing a feed stream which comprises water and which is rich in butene-1, a gaseous recycle stream comprising hydrogen, and a fractionation column overhead stream comprising butene-1 and butene-2 into an isomerization zone operated at isomerization conditions and thereby forming an isomerization zone effluent stream which comprises water, hydrogen, butene-1 and butene-2; condensing at least one-half of the butylenes in the isomerization zone effluent stream and then separating the isomerization zone effluent stream into a hydrogen-rich vapor-phase stream, a liquid-phase hydrocarbon stream comprising butene-1 and butene-2, and a liquid-phase water stream; withdrawing the water stream from the process; passing at least a portion of the vapor-phase stream into the isomerization zone as the previously referred to recycle stream; and separating the liquid-phase hydrocarbon stream in a fractionation column to thereby form the previously referred to fractionation column overhead stream and a fractionation column bottoms stream which is rich in butene-2.

The isomerization zone preferably comprises a single fixed bed reactor although two or more reactors could be employed if desired. The isomerization of light olefins is a quite mild reaction and available catalysts are highly stable. Facilities for the regeneration or replacement of catalyst are therefore not necessary. Within the isomerization zone, the entering reactants are contacted with the catalyst at isomerization conditions in a manner which effects a significant conversion of the feed olefinic hydrocarbon to the product olefinic hydrocarbon. A broad range of light olefin isomerization conditions includes a temperature of about 50° to about 250° C., a pressure of about atmospheric to 800 psig and a liquid hourly space velocity (LHSV) based on fresh feed of between 0.5 and 10.0. If the isomerization zone and the column are equivalent pressures, then the pressure employed in the isomerization zone is limited in part by the increased costs of building fractionation columns designed for high operating pressures and, at the other end of the pressure spectrum, by the costs of condensing the light hydrocarbons at low pressures via refrigeration. The molal hydrogen to hydrocarbon ratio maintained in the isomerization zone may range from about 0.02:1.0 to 1.0:1.0 or higher. A more preferred range of isomerization conditions includes an inlet temperature between about 75° and 160° C., a pressure between 50 and 300 psig and an LHSV between 1.0 and 5.0. The pressure within the isomerization zone is preferably close to the pressure within the fractionation column, with some pressure difference due to inherent pressure drops required to drive vapor flow being acceptable. However, the process may be operated with either the fractionation column or the isomerization reactor being operated at a substantially higher pressure. This would be accomplished by either compressing the overhead vapor stream of the fractionation column or by pressurizing the separator hydrocarbon liquid stream into the fractionation column.

The isomerization reactor may be loaded with any commercially acceptable olefin isomerization catalyst of suitable activity and stability. Such catalysts are known to those skilled in the art and are available from catalyst manufacturing concerns. The preferred catalyst comprises a catalytically effective amount of a Group VIII metal and a solid porous refractory support, also referred to as a carrier material. The support material may be one of the aluminas, a zeolite or a similar material. The catalyst may be in the form of spheres, pellets or an extrudate and the metal component may be added in one of the known manners such as cogelation or impregnation onto formed support particles. An especially preferred catalyst is described in U.S. Pat. No. 3,821,123. This catalyst is produced by forming an initial composite comprising nickel and the support material, sulfiding the composite until it contains at least 0.9 mole of sulfur per mole of nickel and then stripping sulfur from the composite until it contains less than 0.55 mole of sulfur per mole of nickel. Further details on the preferred catalyst are provided in the patent.

The process of the subject invention is further illustrated in the following example which is based on the projected operation of a commercial scale unit. The feed stream contains approximately 15,600 pounds per hour (lb/hr) of butene-1, 3,600 lb/hr or normal butane, 825 lb/hr of isobutane, 1,480 lb/hr of butene-2, 1,980 lb/hr of isobutylene and 9 lb/hr of water. This feed stream is combined with the recycle vapor stream and the fractionation column overhead vapor stream and then heated and passed into a fixed bed reactor containing a sufficient amount of catalyst to result in a liquid hourly space velocity of 2.0 based on the feed stream. The isomerization reactor is operated at a pressure of about 200 psig and with an inlet temperature between 100° and 150° C. Sufficient hydrogen is charged to the process and recirculated by means of a compressor to maintain a total hydrogen to hydrocarbon ratio in the isomerization reactor of at least 0.3:1.0. The effluent of the isomerization reactor is passed into a vapor-liquid separator operated at a temperature of about 35° C. at a pressure near 100 psig. Except for a very small drag stream the vapor phase present in the separator is recycled to the isomerization reactor by means of a compressor. Water is withdrawn from the overhead vessel as it accumulates by means of a level control system. The entire hydrocarbon liquid phase collected in the separator is passed onto the top tray of a single fractionation column at the rate of about 30,500 lb/hr as the feed to this column. The fractionation column separates the entering hydrocarbons and any water dissolved in the hydrocarbons into an overhead vapor stream, which contains essentially all of the water which enters the column, and a net bottoms stream. The entire overhead vapor stream is passed into the isomerization reactor. The net bottoms stream of the column has a flow rate of approximately 23,500 lb/hr and contains about 15,030 lb/hr of butene-2 and 2,050 lb/hr of butene-1. The flow rate of the net bottoms stream is essentially the same as the flow rate of the feed stream, and all components of the feed stream except butene-1 are not significantly affected by the process.

I claim as my invention:
1. A hydrocarbon conversion process which comprises the steps of:
    (a) passing a feed stream which comprises water and a first acyclic olefinic hydrocarbon, a recycle stream comprising hydrogen and the first acyclic olefinic hydrocarbon, and a fractionation column overhead stream comprising the first acyclic olefinic hydrocarbon and a second acyclic olefinic hydrocarbon which is an isomer of the first acyclic olefinic hydrocarbon into an isomerization zone containing a catalytically effective amount of a Group VIII metal deposited on a solid support material operated at isomerization conditions and thereby forming an isomerization zone effluent stream which comprises hydrogen, water and the first and the second acyclic olefinic hydrocarbons;
    (b) partially condensing and then separating the isomerization zone effluent stream in a separation zone into a vapor-phase stream comprising hydrogen, a liquid-phase hydrocarbon stream comprising the first and the second acyclic olefinic hydrocarbons and a liquid-phase water stream;
    (c) withdrawing the water stream from the process;
    (d) passing at least a portion of the vapor-phase stream into the isomerization zone as the previously referred to recycle stream; and,
    (e) passing the liquid-phase hydrocarbon stream into a fractionation column wherein the liquid-phase hydrocarbon stream is separated into the previously referred to fractionation column overhead stream and a fractionation column bottoms stream which is rich in the second acyclic olefinic hydrocarbon.
2. The process of claim 1 further characterized in that the first acyclic olefinic hydrocarbon is a butene.
3. The process of claim 1 further characterized in that the first acyclic olefinic hydrocarbon is an amylene.
4. The process of claim 1 further characterized in that the first acyclic olefinic hydrocarbon is butene-1.
5. A butene isomerization process which comprises the steps of:
    (a) passing a feed stream which comprises water and which is rich in butene-1, a gaseous recycle stream comprising hydrogen, and a fractionation column overhead stream comprising butene-1 and butene-2 into an isomerization zone containing a catalytically effective amount of a Group VIII metal deposited on a solid support material operated at isomerization conditions and thereby forming an isomerization zone effluent stream which comprises water, hydrogen, butene-1 and butene-2;

(b) condensing at least one-half of the butylenes in the isomerization zone effluent stream and then separating the isomerization zone effluent stream into a hydrogen-rich vapor-phase stream, a liquid-phase hydrocarbon stream comprising butene-1
(c) withdrawing the water stream from the process;
(d) passing at least a portion of the vapor-phase stream into the isomerization zone as the previously referred to recycle stream; and,
(e) separating the liquid-phase hydrocarbon stream in a fractionation column to thereby form the previously referred to fractionation column overhead stream and a fractionation column bottoms stream which is rich in butene-2.

6. The process of claim 5 further characterized in that the feed stream also comprises butene-2 and isobutylene.

7. The process of claim 6 further characterized in that the feed stream is heated by heat exchange against the fractionation column bottoms stream and the isomerization zone effluent stream prior to being passed into the isomerization zone.

* * * * *